United States Patent [19]

Pâques

[11] Patent Number: 5,015,583

[45] Date of Patent: May 14, 1991

[54] PROCESS FOR THE PURIFICATION OF PLASMINOGEN ACTIVATORS (PA)

[75] Inventor: Eric P. Pâques, Marburg, Fed. Rep. of Germany

[73] Assignee: Behringwerke Aktiengesellschaft, Marburg/Lahn, Fed. Rep. of Germany

[21] Appl. No.: 282,906

[22] Filed: Dec. 12, 1988

Related U.S. Application Data

[63] Continuation of Ser. No. 849,718, Apr. 9, 1986, abandoned.

[30] Foreign Application Priority Data

Apr. 11, 1985 [DE] Fed. Rep. of Germany ....... 3512910

[51] Int. Cl.$^5$ .............................................. C12N 9/48
[52] U.S. Cl. .................................. 435/212; 424/94.3; 424/94.63; 424/94.64; 435/215; 435/216; 435/219; 435/814; 435/948; 530/380; 530/395; 530/397; 530/399; 530/412; 530/413; 530/417
[58] Field of Search ................. 424/94.3, 94.63, 94.64; 435/212, 215, 216, 219, 814, 948; 530/380, 395, 397, 399, 412, 413, 417

[56] References Cited

U.S. PATENT DOCUMENTS

| Number | Date | Name | Class |
|---|---|---|---|
| 3,920,625 | 11/1975 | Andersson et al. | 530/382 |
| 3,943,245 | 3/1976 | Silverstein | 530/413 |
| 3,998,947 | 12/1976 | d'Hinterland et al. | 530/380 X |
| 4,066,506 | 1/1978 | Johnson et al. | 435/814 X |
| 4,137,127 | 1/1979 | Stocker . | |
| 4,178,439 | 11/1979 | Ayers et al. | 536/59 |
| 4,210,580 | 7/1980 | Amrani | 530/382 X |
| 4,245,051 | 1/1981 | Reich et al. | 435/212 |
| 4,278,594 | 7/1981 | Amrani | 530/382 X |
| 4,317,882 | 3/1982 | Horiguchi et al. | 435/212 |
| 4,326,033 | 4/1982 | Holleman et al. | 435/212 |
| 4,505,893 | 3/1985 | Mori et al. | 424/105 X |
| 4,515,714 | 5/1985 | Kawahara et al. | 530/417 X |
| 4,522,751 | 6/1985 | Linnau et al. | 530/382 X |
| 4,550,080 | 10/1985 | Hasegawa et al. | 435/212 |
| 4,552,760 | 11/1985 | Murakami et al. | 435/212 X |
| 4,568,544 | 2/1986 | Hasegawa et al. | 435/212 X |
| 4,578,218 | 3/1986 | Saundry et al. | 530/383 |
| 4,661,453 | 4/1987 | Pollard | 435/219 X |
| 4,752,603 | 6/1988 | Collen et al. | 514/21 |
| 4,753,879 | 6/1988 | Rosa et al. | 435/212 X |
| 4,882,275 | 11/1989 | Klagsbrun | 530/413 X |
| 4,902,782 | 2/1990 | Gospodarowicz et al. | 530/399 |

FOREIGN PATENT DOCUMENTS

| | | |
|---|---|---|
| 0023860B1 | 2/1981 | European Pat. Off. . |
| 00417660A2 | 12/1981 | European Pat. Off. . |
| 0261941 | 3/1988 | European Pat. Off. ............ 435/212 |
| 2815853A1 | 10/1978 | Fed. Rep. of Germany . |

OTHER PUBLICATIONS

Pacques et al., Thrombosis Research, 42, 797–807 (1986).
Andrade-Gordon et al., Biochemistry, 25, 4033–4040 (1986).
I. Bjork et al., The Physiological Inhibitors of Coagulation and Fibrinolysis, Elsevier North-Holland Biomedical Press, pp. 67–84, 1979.
E. J. McKay et al., J. Lab. Clin. Med., pp. 69–80, Jan. 1980.
M. Miller-Andersson et al., Thrombosis Research, vol. 5, pp. 439–452.
Dirksen et al., "Production of Plasminogen Activator from Monkey Kidney Cell Culture", Thrombosis Research, 19:525–534, 1980.
Shibatini et al., "Purification of High Molecular Weight Urokinase from Human Urine and Comparative Study of Two Active Forms of Urokinase", Thromb Haemostas (Stuttgart) 49(2) 92–95 (1983).
Nielsen et al., "Purification of Zymogen to Plasminogen Activator from Human Gliobastoma Cells by Affinity Chromatography with Antibody", Biochemistry, 21:6410–6415 (1982).
Husain et al., "Rapid Purification of a High-Affinity Plasminogen Activator from Human Blood Plasma by Specific Adsorption on Fibrin/Celite", Proc. Natl. Acad. Sci. U.S.A., 76(7) 4265–4269 (1981).
Chemical Abstracts 90 (3) 245, Abstract 18309a, 1978.
CHA-647,548, Jan. 1985, Pentapharm. .
The Journal of Biochemistry, 92(4) 1129–1140 (1982), Hishikawa. .

Primary Examiner—Howard E. Schain
Attorney, Agent, or Firm—Finnnegan, Henderson, Farabow, Garrett, and Dunner

[57] ABSTRACT

A process is described for the purification of plasminogen activator (PA), wherein a solution containing such as plasminogen activator is brought into contact with a carrier-bound polysulfate of a saccharide or sulfated sugar, the liquid is removed, and the PA bound by this material is eluted.

19 Claims, No Drawings

PROCESS FOR THE PURIFICATION OF PLASMINOGEN ACTIVATORS (PA)

This application is a continuation of application Ser. No. 849,718, filed Apr. 9, 1986, abandoned.

The invention relates to a process for the purification of plasminogen activators (PA). The term plasminogen activator is intended to mean proteins having urokinase and tissue plasminogen activator (t-PA) activity as well as their derivatives obtained by synthetic or genetically engineered processes.

Plasminogen is converted into plasmin by plasminogen activators. Catalysts for this reaction include urokinase and t-PA. The therapeutic use of these activators as fibrinolytics is known. Because of its high affinity for fibrin, t-PA is of particular significance for lysis therapy.

Methods for the isolation and purification of PA from cell culture supernatants and urine have already been described (German Offenlegungsschrift No. 2,815,853, European Patent No. 0,041,766). These processes are complicated and are therefore not suitable for industrial use.

A process for the isolation of t-PA is described in European Patent No. 0,041,766. Zinc chelate Sepharose ®, concanavalin-A-Agarose ® and Sephadex ® G-150 (superfine) are used for this. Each of these purification steps is associated with great disadvantages: zinc and concanavalin A can contaminate the product, and Sephadex ® G-150 (superfine) cannot be used in an industrial process because of its capacity and its flow properties. In European Patent No. 0,023,869, the purification of t-PA with a carrier onto which soluble fragments of fibrin are immobilized by covalent bonding is described. This process is likewise unsuitable for industrial isolation processes.

The object of the present invention is to develop a simple purification process for PA.

It was found, surprisingly, that the abovementioned PA exhibit a high affinity for polysulfates of saccharides or sulfated sugars and a purification of these PA is possible via this type of substance if the latter is bound to a carrier.

The invention therefore relates to a process for the purification of plasminogen activators, which comprises bringing a solution containing one of these activators into contact with a carrier-bound polysulfate of a saccharide or sulfated sugar ("affinity material"), removal of the liquid and elution of the activator bound by this material.

Plasminogen activator is to means a protein having urokinase or tissue plasminogen activator (t-PA) activity as well as synthetic or genetically engineered prepared derivatives.

The plasminogen activator is preferably of human origin.

Preferred is also an embodiment of the invention in which the plasminogen activator is tissue plasminogen activator or a derivative thereof.

The plasminogen activator may preferably also be urokinase or a derivative thereof.

Preferably, impurities bound by the affinity material are removed by washing before the elution of the activator.

Furthermore, a preferred process is one in which the loaded affinity material is freed from impurities using a buffer containing sodium sulfate, ammonium sulfate, NaCl, LiCl or citrate, and the activator is eluted with a buffer solution containing potassium nitrate, ammonium chloride, barium chloride, potassium bromide, calcium chloride, magnesium chloride, potassium thiocyanate, urea or a mixture of these substances.

Insoluble agarose, dextran, acrylamide or polyethylene glycol glycidyl metharylate polymers or a combinaiton thereof may be used, for example, as carrier materials for a covalent coupling of polysulfates of a saccharide or sulfated sugars. Dextran or Agarose matrices are preferred.

The coupling of polysulfates of saccharides or sulfated sugars takes place according to known methods such as, for example, by binding to carrier material preactivated with cyanogen bromide, or by binding to amino-functionalized resin by means of carbodiimide condensation, but preferably by coupling to lysine-functionalized carrier material by means of carbodiimide condensation.

Dextran sulfate, heparan sulfate, chondroitin sulfate, keratan sulfate, dermatan sulfate, pentosan sulfate or Arteparon ®, preferably heparin, may be used as polysulfates of a saccharide or sulfated sugars.

A further advantageous process comprises mixing of the solution containing plasminogen activator with a carrier-bound polysulfate of a saccharide or sulfated sugar, preferably heparin-lysine-Sepharose, washing of the loaded affinity material with a buffer of pH 3 to 9 which, where appropriate, contains NaCl, elution of the impurities bound on the resin with a buffer of pH 3 to 9 containing sodium sulfate, ammonium sulfate, NaCl, LiCl or citrate, preferably with a 0.1 to 2 mol/l citrate solution of pH 3 to 9, preferably with 0.5 mol/l citrate pH 3.5 to 6, and elution of the plasminogen activator with a buffer of pH 3 to 9 containing $KNO_3$, KSCN, $NH_4Cl$, $CaCl_2$, $MgCl_2$, KBr, $BaCl_2$ or urea, preferabnly 1 to 2 mol/l KSCN, preferably pH 5–8, containing, where appropriate, detergents, preferably 0.1 to 1 g/l Tween ® 80 (poloyoxyethylene sorbitan monooleate).

In a particularly preferred embodiment, the process may be such that the solution containing PA, for example melanoma cell culture supernatant or urine, demineralized where appropriate, is mixed with heparin-, dextran sulfate- or pentosan sulfate-Sepharose ®, preferably heparin-Sepharose ®, heparin-lysine-Sepharose ® being preferred, preferably in a ratio of 10 l cell culture supernatant to 100 g affinity material, the resin is freed from impurities using a 0.1 to 2 mol/l citrate solution, pH 3–9, preferably with 0.5 mol/l citrate, pH 3.5–6, and plasminogen activator is eluted with a buffer containing 1–2 mol/l KSCN, pH 5–8, where appropriate containing 0.1–1 g/l Tween ® 80.

In another, particularly preferred, embodiment the process may be such that PA is eluted with a buffer solution, containing 1 to 2 mol/l $CaCl_2$ with a pH of 4 to 9, preferably with a 2 mol/l $CaCl_2$ solution of pH 5 to 8, containing, where appropriate, 0.1 to 1 g/l Tween ® 80.

This process is distinguished by the fact that, with one purification step, PA can be obtained in a degree of purity and specific activity which are obtained according to conventional processes only after several purification steps.

A further embodiment of the invention is a tissue plasminogen activator or a derivative thereof obtained by the disclosed process.

Still another embodiment of the invention is urokinase or a derivative thereof obtained by the disclosed process.

The invention will be illustrated by the following examples.

EXAMPLE 1

10 l of cell culture supernatant of melanoma cells producing t-PA were mixed, with stirring, with 100 g of a heparin-Sepharose ® at room temperature. After removal of the protein liquid, the affinity material was washed with 0.1 mol/l tris.HCl, 0.1 mol/l NaCl, pH 7.5 containing 0.1% Tween ® 80 and subsequently freed from impurities with 0.5 mol/l citrate pH 5.0. The PA was eluted with a buffer containing 0.1 mol/l tris.HCl, 2 mol/l KSCN and 0.01% Tween ® 80, pH 7.5. The eluate was dialyzed, concentrated and tested for t-PA activity. Of the t-PA activity present in the starting solution, 99% were bound to heparin-Sepharose. After elution, approximately 90% of the t-PA activity were recovered.

A polyacrylamide gel electrophoresis showed two protein bands of different molecular weight. One band could be immunologically assigned to t-PA.

EXAMPLE 2

10 l of cell culture supernatant were treated in the same manner as indicated in Example 1, and subsequently eluted with a 2 mol/l CaCl$_2$ solution containing 0.1 mol/l tris, pH 8.0, and 0.1% Tween ® 80. The results were comparable with those indicated in Example 1.

EXAMPLE 3

Salts were removed from 10 l of urine by dialysis, and subsequently, with stirring, 100 g of a heparin-Sepharose ® were added, at room temperature. After removal of the protein liquid, the affinity material was washed with 0.1 mol/l tris.HCl pH 7.5 and then eluted with a buffer solution containing 2 mol/l KSCN, 0.1 mol/l tris.HCl, pH 7.5. 80% of the starting activity was bound to heparin-Sepharose. After elution approximately 80% of the urokinase activity were recovered.

EXAMPLE 4

10 l of a cell culture supernatant of melanoma cells producing t-PA were mixed with 500 g pentosan sulfate-Sepharose and processed as in Example 3. Approximately 80% of the activity were bound on the resin.

I claim:

1. A process for the purification of a tissue plasminogen activator, which comprises bringing a solution containing tissue plasminogen activator or derivatives thereof into contact with a carrier-bound affinity material selected from the group consisting of polysulfates of a saccharide and sulfated sugars to create a loaded affinity column, removing the impurities from the loaded affinity column, and eluting the tissue plasminogen activator bound by the affinity material.

2. The process as claimed in claim 1, wherein the polysulfate of a saccharide or sulfated sugar is bound to a carrier via lysine.

3. The process as claimed in claim 1, wherein the polysulfate of a saccharide is heparin.

4. The process as claimed in claim 1, wherein the carrier is agarose.

5. The process as claimed in claim 1, wherein before elution of the plasminogen activator the bound impurities are removed by washing the affinity material with a buffer solution containing at least one of sodium chloride, sodium sulfate, ammonium sulfate, lithium chloride or alkali metal citrate.

6. The process as claimed in claim 1, wherein before the elution of the plasminogen activator the bound impurities are removed by washing the affinity material with a 0.1 to 2 mol/l citrate solution, pH 3-9.

7. The process as claimed in claim 1, wherein before elution of the plasminogen activator the bound impurities are removed by washing the affinity material with a 0.4 to 0.6 mol/l citrate solution, pH 3.5-6.

8. The process as claimed in claim 1, wherein the loaded affinity material is freed from impurities with a buffer, and the plasminogen activator is eluted with a solution of potassium nitrate, ammonium chloride, calcium chloride, magnesium chloride, potassium bromide, barium chloride, urea or potassium thiocyanate or a mixture of these substances.

9. The process as claimed in claim 1, wherein the loaded affinity material is freed from the impurities with a buffer, and the plasminogen activator is eluted with a buffer solution containing 0.5 to 2 mol/l KSCN, pH 4-9.

10. The process as claimed in claim 1, wherein the loaded affinity material is washed with a buffer of pH 4-9, the bound impurities are removed by washing the affinity material with a 0.4 to 0.6 mol/l alkali metal citrate solution, pH 3.5-6, and the plasminogen activator is eluted with a buffer solution containing 0.5 to 2 mol/l KSCN, pH 4-9.

11. The process of claim 5, wherein the buffer solution further comprises 0.1 to 1 g/l polyoxyethylene sorbitan monooleate.

12. The process of claim 6, wherein the citrate solution further comprises about 0.1 to about 1.0 g/l polyoxyethylene sorbitan monooleate.

13. The process of claim 7, wherein the citrate solution further comprises about 0.1 to about 1.0 g/l polyoxyethylene sorbitan monooleate.

14. The process of claim 8, wherein the solution further comprises about 0.1 to about 1.0 g/l polyoxyethylene sorbitan monooleate.

15. The process of claim 9, wherein the buffer solution further comprises about 0.1 to about 1.0 g/l polyoxyethylene sorbitan monooleate.

16. The process of claim 10, wherein the buffer used to wash the loaded affinity material further comprises NaCl.

17. The process of claim 16, wherein the citrate solution further comprises about 0.1 to about 1.0 g/l polyoxyethylene sorbitan monooleate.

18. The process of claim 17, wherein the buffer solution used to elute the plasminogen activator further comprises about 0.1 to about 1.0 g/l polyoxyethylene sorbitan monooleate.

19. The process of claim 2, wherein the polysulfate of a saccharide or sulfated sugar is heparin.

* * * * *